(12) United States Patent
Kindlein

(10) Patent No.: US 7,697,147 B2
(45) Date of Patent: Apr. 13, 2010

(54) APPARATUS AND METHOD FOR THE REPRESENTATION OF AN AREA ON THE SURFACE OF A PATIENT'S BODY

(75) Inventor: Johann Kindlein, Luneburg (DE)

(73) Assignee: LAP GmbH Laser Applikationen, Luneburg (DE)

( * ) Notice: Subject to any disclaimer, the term of this patent is extended or adjusted under 35 U.S.C. 154(b) by 1 day.

(21) Appl. No.: 12/132,874

(22) Filed: Jun. 4, 2008

(65) Prior Publication Data

US 2009/0251709 A1    Oct. 8, 2009

(30) Foreign Application Priority Data

Mar. 4, 2008  (DE) ........................ 10 2008 012 496

(51) Int. Cl.
*G01B 11/24* (2006.01)
(52) U.S. Cl. ...................................... 356/608; 356/601
(58) Field of Classification Search ......... 356/600–608, 356/614, 620–623; 250/559.24, 221, 559.4, 250/559.29, 559.3, 370.09, 370.08, 370.1; 378/20, 206, 62, 63, 64, 65
See application file for complete search history.

(56) References Cited

U.S. PATENT DOCUMENTS 3,625,618 A * 12/1971 Bickel ........................ 356/606

5,690,107 A * 11/1997 Hofmann ..................... 600/407
6,088,106 A    7/2000 Rockseisen

FOREIGN PATENT DOCUMENTS

| DE | 44 18 216 A1 | 11/1995 |
|----|--------------|---------|
| DE | 44 21 315 A1 | 12/1995 |
| DE | 195 24 951 A1 | 1/1997 |

* cited by examiner

*Primary Examiner*—Gregory J Toatley, Jr.
*Assistant Examiner*—Tri T Ton
(74) *Attorney, Agent, or Firm*—Vidas, Arrett & Steinkraus, P.A.

(57) ABSTRACT

An apparatus for the representation of an area on the three-dimensional surface of a patient's body, with a control device which provides three-dimensional coordinates of at least one area to be represented on the surface of the patient's body, wherein the area pre-sets a desired intersection area of a radiation area on the surface of the patient's body, characterized in that at least one projection device featuring a laser is provided, by which the desired intersection area can be projected to the three-dimensional surface of the patient's body on the basis of the provided coordinates, while at least one laser beam generated by the laser can be guided along the contour of the desired intersection area sufficiently rapidly, so that the impression of a closed contour around the desired intersection area results.

27 Claims, 4 Drawing Sheets

APPARATUS AND METHOD FOR THE REPRESENTATION OF AN AREA ON THE SURFACE OF A PATIENT'S BODY

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to an apparatus and a method for the representation of an area on the surface of a patient's body, and relates to the field of radiation therapy with ionising radiation for treating cancer. In this, usually plural rays from different directions are directed to the body to be treated, so that they intersect in an isocentre. Here acts the summed-up radiation dose of the different ionising rays directed to the isocentre. In this way, the adverse effect to the surrounding tissue is minimised.

As the first step of a radiation therapy, a computer tomography (CT) mapping of the patient positioned and fixed on a positioning aid, like a treatment table, is established. Based on this mapping, a 3D-model of the patient is made and the tumour to be treated is localised and an irradiation plan is set up. This comprises contouring the target volumes as well as the calculation of the dose for the irradiation, and in this the determination of the number and location of the radiation areas of the irradiation machine in particular, so that the tumour is irradiated as desired.

During the execution of this irradiation planning, the patient is no more on the positioning aid. Furthermore, a plurality of irradiation dates (usually up to 30 fractions) takes usually place in the frame of such a radiation therapy. Therefore, a transfer of the radiation areas calculated on the basis of the established 3D-model of the patient to the real patient is repeatedly necessary. This step is also called "simulation". In particular, the patient must be reproducibly laid on the treatment table such as he/she lay when the CT mapping was established.

In order to do this, it is known to perform a positioning of the patient by means of 3D bone radiography ("Cone Beam"), wherein bones of the patient constitute the reference points for an alignment of the patient, for instance. The advantage of this method is a high accuracy. In addition, no reference marks or the like have to be affixed on the patient's skin. The disadvantage of this method is a high x-ray radiation dose for the patient, because the x-ray positioning is required before each treatment fraction. Thus, in the frame of a radiation therapy, this may usually take place up to 30 times. This radiation dose applied to the body in a great volume can induce a new cancer again in the long term, in younger patients in particular.

According to a known alternative method, the patient can be positioned on the positioning aid by means of three reference points on its skin, which are formed by suitable retro reflectors, for instance. Such a method is known from DE 44 18 216 A1, the entire contents of which is incorporated herein, for instance. After performing the irradiation planning, the intersection points of the irradiation areas with the surface of the skin which are necessary for the desired irradiation are calculated. The intersection points are then at hand in the form of a 3D coordinate table. After newly positioning the patient on the basis of the three reference marks, the coordinates from the table can then be represented on the body surface of the patient one after the other with a laser system. The approach to the coordinates can be controlled by an operator through an infrared remote control for instance. The respective points represented by the laser are then manually drawn in on the skin of the patient, with a pencil for instance. The desired intersection area for the irradiation results by connecting the points.

Such a method is known from DE 44 21 315 A1 or DE 195 24 951 A1, the entire contents of which is incorporated herein by reference, for instance. The laser device used for this consists of five motor movable lasers in particular, wherein two lasers adjustable in the height direct a horizontal line along the treatment table to the patient, at the right and at the left side from the treatment table, respectively. The remaining three lasers are mounted in a plate which is situated above the treatment table, a CT table for instance. In this, one laser is movable transversely to the table's long side direction and directs a line along the table to the patient. The two remaining lasers in the plate are coupled with each other and direct a common line to the patient, transversely to the table's alongside. By the coupling of two lasers, even such coordinates can be represented on the skin of the patient which otherwise would be shaded below the transverse diameter of the patient. With the described system, it is possible to approach almost arbitrary coordinates on the skin of the patient, wherein one coordinate is always indicated by a cross of two laser lines. Such a laser system is offered by the applicant under the name "Dorado CT4".

However, the described method is relatively time-consuming and thus expensive, because usage time in the CT-room is very expensive. In addition to this, manual drawing in the points is not always sufficiently accurate, depending on the adiposity of the patient in particular. In particular, skin marks can shift. Therefore, marks of the intersection areas on the skin are performed only partially in practice. Correspondingly, the correct irradiation of the patient is not always secured in a sufficiently accurate way.

The simulation is not only an assignment of the irradiation plan to the patient, but also an important element in the context of the quality assurance. The irradiation plan is checked for its plausibility for the last time before the therapy and it is determined whether the ray areas can be reproducibly adjusted to the desired planned target volume.

Based on the clarified state of the art, the present invention is based on the objective to provide an apparatus and a method of the kind indicated in the beginning, by which the simulation process of the radiation therapy is possible in a simple, more rapid and precise way and without danger for the health of the patient at the same time.

BRIEF SUMMARY OF THE INVENTION

For an apparatus for the representation of an area on the three-dimensional surface of a body, a patient's body in particular, with a control device which provides three-dimensional coordinates of at least one area to be represented on the surface of patient's body, wherein the area pre-sets a desired intersection area of a radiation area on the surface of the patient's body, the objective is resolved according to the present invention in that at least one projection device featuring a laser is provided, by which the desired intersection area can be projected to the three-dimensional surface of the patient's body on the basis of the provided coordinates, while at least one laser beam generated by the laser can be guided along the contour of the desired intersection area sufficiently rapidly, so that the impression of a close contour around the desired intersection area results.

For a method for the representation of an area on the three-dimensional surface of a body, a patient's body in particular, wherein three-dimensional coordinates of at least one area to be represented on the surface of the patient's body are provided by a control device, wherein the area pre-sets a desired intersection area of a radiation area on the surface of the patient's body, the objective is resolved according to the present invention in that with at least one projection device featuring a laser, the desired intersection area is projected to the three-dimensional surface of the patient's body on the basis of the provided coordinates, while at least one laser beam generated by the laser is be guided along the contour of the desired intersection area sufficiently rapidly, so that the impression of a close contour around the desired intersection area results.

The control device of the projection device provides also the three-dimensional coordinates of the surface of the patient's body. In this, the area to be represented (the desired intersection area) is selected such that the envisioned body region is irradiated by the radiation in the manner desired and calculated in the context of the irradiation planning. In this, the area is depending on the form of a multi leaf collimator of an irradiation machine, a linear accelerator for instance, and/or on the position of the isocentre of a tumour to be treated. In this, plural areas can be represented in particular, in the case that plural rays are used for the treatment which must intersect in an isocentre situated in the body of the patient. In this, the basic idea of the invention is to approach the 3D coordinates for the desired intersection area, provided by the control device and determined in the frame of the irradiation planning, one after the other by means of a laser projector as the optical system. In doing so, the coordinate points are approached by the laser beam so rapidly that for a human spectator, a closed contour or a closed silhouette appears on the skin around the desired intersection area. Thus, a direct correlation between the virtual patient in the computer, on the basis of a CT image for instance, and the real patient on the CT table is established. The advantage of this "virtual simulation" is a particularly rapid and simple representation of the desired radiation areas on the skin, or a marking of the patient, with a pencil for instance, which is possible in a correspondingly rapid and simple way, respectively, on the basis of the laser projection. In particular, no time-consuming manual approach to coordinates from the table of the irradiation planning is necessary. Instead, these coordinates are approached automatically by the laser projector and thus the area is projected to the body surface. The use of x-rays hazardous for the health is not necessary.

The apparatus according to the present invention can be arranged in the treatment room with the irradiation machine, a linear accelerator (LINAC) for instance, in the CT room with a CT machine or in a separate room. An irradiation machine or a CT might also be envisioned for the apparatus in a corresponding manner. In particular, the coordinates of the desired intersection area provided by the control device can be established on the basis of a CT image of the patient. Furthermore, the apparatus can feature a computer system with a graphic image representation and software (algorithms) for the virtual simulation of the irradiation of a patient on the basis of CT images with interfaces for the transmission of image data, irradiation data, irradiation area contours and so on. This computer system may be a part of the control device. The different devices of the apparatus can be connected via a local network. The exchange of the data can proceed in a particularly simple manner via the Digital Imaging and Communications in Medicine (DICOM and DICOM RT) standard. For instance, the system can grant different functionalities and rights in different rooms. For purposes of quality control, all the data files can be filed in a server file.

Even according to the present invention, marking of the patient with a pencil or the like along the projected silhouette is possible, but not necessarily required. However, on the basis of the projection, the represented desired intersection area can be marked on the skin in a particularly simple manner, drawn in with a pencil or the like, for instance. In this case, the apparatus has not to be arranged in the irradiation room. Instead, the simulation may take place in a separate room, the use of which is less expensive than that of the irradiation or CT room. In addition, the irradiation or CT room has not to be rebuilt by the installation of the apparatus of the invention in this case. After marking the patient, the light area simulating the treatment area can be directed to the patient in the treatment room with the irradiation machine and the patient can be aligned such that the mark and the light area are coincident. This may take place manually or automatically, as will be explained in more detail below.

In a per se known manner, the alignment of the patient before the projection of the area can take place by means of three reference marks, for instance, which are recognised by a laser, for instance, and by subsequently aligning the patient via a control of the positioning aid in particular, as is known from DE 44 18 216 A, the entire contents of which is incorporated herein by reference, for instance.

The projection can take place in a particularly simple manner when the projection device has at least two rotatable mirrors, by which the laser beam can be reflected to the surface of the patient's body and can be guided along the contour of the desired intersection area. For instance, the mirrors may be electrically driven galvanometer mirrors. With this embodiment, a particularly high precision is achieved in the projection.

In order to have the system executable, a calibration of the projection device must be performed by providing calibration coordinates which are addressed by the control device and thus the calibration parameters are determined. At least six points must be addressed. In this, one of the calibration points which is used for calibration lays in the isocentre of a CT-machine or a linear accelerator.

The apparatus can feature an irradiation machine for generating ionising radiation for the radiation therapy, wherein a light radiation corresponding to the radiation generated by the irradiation machine can be generated by the irradiation machine, and wherein the apparatus has a sensor device, by which the desired intersection area and a light intersection area of the light radiation of the irradiation machine on the surface of the patient's body can be acquired. In this embodiment, a manual marking of the patient, with a pencil for instance, is not necessarily required. In particular, the apparatus is then arranged in the same room as is the irradiation machine used for the irradiation. The irradiation machine serves for tumour treatment and may be a linear accelerator, for instance. The sensor device may be a camera, for instance. In this, different coordinate systems may be valid for the desired intersection area and the light intersection area. The light intersection area is represented by visible light in particular, and it simulates the treatment area. In this, an analysing device can be provided, which is designed to detect a deviation between the desired intersection area and the light intersection area. For instance, the analysing device can be integrated into the control device. It may comprise an image analysing software for 3D replication or for overlapping ("matching") the desired intersection area with the light intersection area.

The apparatus according to the present invention can feature a positioning aid, accommodating the patient's body, mounted adjustably along at least three degrees of freedom by means of suitable adjustment drives, a treatment table in particular. In particular, the degrees of freedom may be three axis, aligned orthogonally with respect to each other. An adjustability of the table can also be possible along more than three degrees of freedom, in 6 degrees of freedom for instance, so that a rotation of the positioning aid is possible, for instance. Thus, the positioning aid has sufficient degrees of freedom so that the patient to be treated can be brought into the required position which he/she already had in the irradiation planning, in the establishment of the CT image for making a 3D model of the patient in particular.

The analysing device according to the present invention can be designed to determine a position of the positioning aid necessary for the coincidence between the desired intersection area and the light intersection area. Furthermore, it can be designed to control the adjustment drives such that the positioning aid is moved into the necessary position. In this, a matching of the areas acquired by the sensor device is at hand only then and merely then when the patient is in the same position as in the radiation planning. The analysing device has a corresponding analysing algorithm for bringing the two 3D contours into overlapping by a dislocation of the positioning aid. In this, the parameters for adjusting the positioning aid can be transmitted to the adjustment drives automatically or after input by an operator.

Of course, the described overlapping of the 3D contours and the subsequent positioning of the positioning aid can also be performed in an analogous way on the basis of a comparison between a desired intersection area manually drawn in on the patient, a pencil mark for instance, and the light intersection area of the irradiation machine. Then, a projection of the desired intersection area in the irradiation room is no more necessary.

According to a further embodiment of the present invention, a device for determining the topography of a patient's body present on the positioning aid can be provided, which has at least one laser scanner by which a laser line can be directed to the patient's body, and at least one capture device, by which the laser line reflected by the patient's body can be acquired. Such a laser scanning system is offered by the applicant under the name "Galaxy", for instance. In this, the laser line can be successively guided across the patient's body with the laser scanner, wherein the capture device, a corresponding sensor (matrix sensor) for instance, successively acquires the laser lines reflected by the patient's body. From the sensor data, the topography of the entire body or of part of a patient's body can then be determined. The wavelength of the laser scanning system can be selected to be different from the wavelength of the projection device which projects the desired intersection area to the surface, in order to avoid undesired influences. Furthermore, a topography analysing unit can be provided, which is designed to determine the topography of the patient's body from the data acquired by the capture device, to compare it with a desired topography and to determine a position of the positioning aid necessary for the coincidence between the measured topography and the desired topography by means of the comparison. For instance, the desired topography may originate from a CT image or a recorded reference topography established in the frame of the irradiation planning. The topography analysing unit can be designed to move or to address, respectively, the positioning aid or the adjustment drives of the positioning aid, respectively, in such a way that the positioning aid is moved into the required position. With this embodiment, a particularly accurate positioning of the patient is possible without that the positioning must take place on the basis of reference points formed by retro reflectors or the like. In addition, in this embodiment, the projection of the desired intersection area to the patient's body can be performed in a room which is separated from the treatment and/or CT room, wherein a precise and reliable positioning of the patient and with it of the projection of the desired intersection area is achieved anyhow and can be visually checked by the medical personnel.

According to the present invention, plural laser projection devices, two for instance, may be provided in order to be able to represent the desired intersection area on all the positions of the patient's body. Thus, for instance, at least one projector arranged above the positioning aid can be provided at a time on the left and on the right side of the positioning aid accommodating the patient. However, it is also possible that the projection device is arranged to be movable along a substantially circular course around a positioning aid accommodating the patient's body. In particular, one laser projector is sufficient in this case, which can be moved on a circular rail above and/or below the positioning aid, so that it can reach all the body regions of a patient and represent the area on the same. The respective holding positions of the projector on the rail required for representing a calculated area can be determined by the control device or the respective implemented virtual simulation program, and a drive device for moving the projection device can be addressed in a corresponding manner.

According to a further embodiment of the present invention, a device for determining a three-dimensional surface shape of a patient's body situated on the positioning aid in real time or nearly real time can be provided, wherein three-dimensional surface data determined by the device can be forwarded to the control device in real time or nearly real time. Corresponding systems are provided for the surface acquisition in real or nearly real time. By the breathing of the patient, his/her surface is changed, in the region of the thorax in particular. This can lead to undesired position deviations of the irradiation areas. According to this embodiment of the invention, the control device and with it the laser projector which projects the desired intersection area to the body surface knows the respective surface of the patient in real time or nearly real time, thus even at a change due to a breathing activity, for instance. The device for determining the three-dimensional surface shape of the patient's body in real time or nearly real time can have at least one laser, by which at least one laser line can be directed to the patient's body, and at least one matrix sensor, by which the laser line reflected by the patient's body can be detected. The matrix sensor is a sensor with a plurality of sensor rows arranged parallel in particular. In particular, the same may run perpendicular to the laser line or lines, respectively, which are imaged on the patient surface. In a change of the surface of the patient, a corresponding change of the signal results. From this, the determination of the surface shape is possible in the region of the thorax, for instance. A realisation for implementing this method is known from U.S. Pat. No. 6,088,106 A. In order to avoid undesired influences, the wavelength of the laser line of the surface acquisition system can be selected to be different from the wavelength of the projection device which projects the desired intersection area to the surface (and optionally even differently from the wavelength of a laser scanning system).

On the basis of the surface acquisition in real time or nearly real time, the control device can be designed to address the projection device such that the same projects the desired intersection area to the three-dimensional surface position of the patient's body only in a pre-set surface position of the patient's body. In particular, a control corresponding to the breathing cycle of the patient is possible in this. Thus, the area is projected to the body only in a certain position of the patient surface, in a certain breathing position for instance. Thus, there is a controlled ("gating") projection. In this way it is made sure that there is no corruption of the result by an undesired deviation of the projected area from the desired intersection area through the breathing of the patient.

It is also possible to design the control device to acquire the coordinates of the surface of the patient's body and of the desired intersection area provided to the projection device depending on the respective surface of the patient's body in real or nearly real time. Thus, in this embodiment, there is a new acquisition and a new calculation of the 3D coordinates in real time or nearly real time, so that the wanted desired intersection area is projected at each surface shape.

The apparatus according to the present invention can be suited for the execution of the method according to the present invention in particular. Correspondingly, the method of the invention can be performed with the apparatus of the invention.

BRIEF DESCRIPTION OF THE SEVERAL VIEWS OF THE DRAWINGS

An example of the realisation of the invention will be explained in more detail in the following by means of a drawing. Schematically shows.

DETAILED DESCRIPTION OF THE INVENTION

Figure 1:
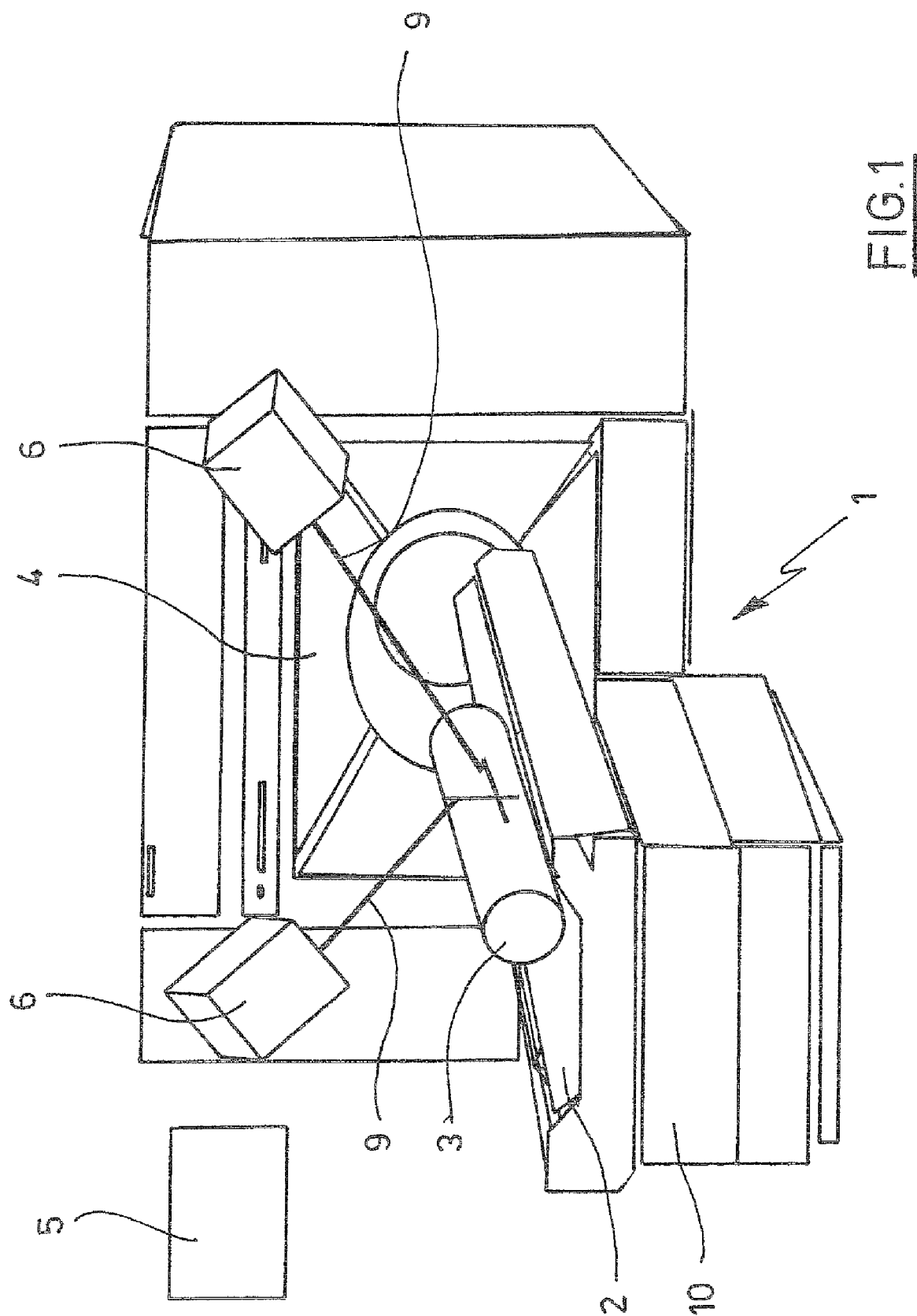
FIG. 1 an apparatus according to the present invention according to a first embodiment, FIG. 2 an apparatus according to the present invention according to a second embodiment, FIG. 3 an apparatus according to the present invention according to a third embodiment, and FIG. 4 a schematic representation for illustrating the functionality of the apparatus according to the present invention.

While this invention may be embodied in many different forms, there are described in detail herein a specific preferred embodiment of the invention. This description is an exemplification of the principles of the invention and is not intended to limit the invention to the particular embodiment illustrated As far as not indicated otherwise, same reference signs indicate same objects in the figures. In FIG. 1, an apparatus 1 of the invention for the representation of an area on the surface of a patient's body is depicted. The apparatus has a positioning aid 2, mounted adjustably along at least three axis by means of adjustment drives not shown in more detail, a CT table 2 in the example. On the CT table 2, a body 3, a patient's body 3 for instance, is depicted in a very schematic manner. Further, the apparatus 1 comprises a computer tomography machine 4 arranged in a housing. In this CT machine 4, CT recordings and a three dimensional sectional image of a patient based on these can be made in a per se known manner. Thereafter, a detection of the target volumes for the irradiation with ionising radiation takes place in the frame of an irradiation planning. In an analysing device integrated into the control device 5, the coordinates of a corresponding desired intersection area of a therapy area on the surface of the patient's body 3 envisioned for the radiation therapy are calculated on the basis of target volumes established by the 3D sectional image of the patient. Subsequently, the control device 5 provides these 3D coordinates to projection devices (laser projectors).

The apparatus depicted in FIG. 1 comprises two projection devices 6 each having a laser. Via a connection line not shown in more detail, the coordinates are supplied from the control device 5 to at least one of the projection devices 6. In this, the projection devices 6 are arranged stationarily in the room accommodating the apparatus and provided in such an angle to the patient's body that all the regions of the patient's body 3 can be commonly reached by the lasers of the projection devices 6. In this, the coordinates are transmitted by the control device 5 to that projection device 6 which covers the respective desired body region of the patient 3. Then, the desired intersection area is projected with the provided coordinates to the surface of the patient body 3 by the projection device 6, while a laser beam 9 generated by the laser is guided sufficiently rapidly along the contour of the desired intersection area, so that the impression of a closed contour around the desired intersection area results for a human observer. The laser beam 9 is guided along the contour of the desired intersection area via two electrically driven galvanometer mirrors. Thereafter, the desired intersection area 18 can be marked on the skin, manually for instance, with a pencil or the like e.g.

Figure 2:
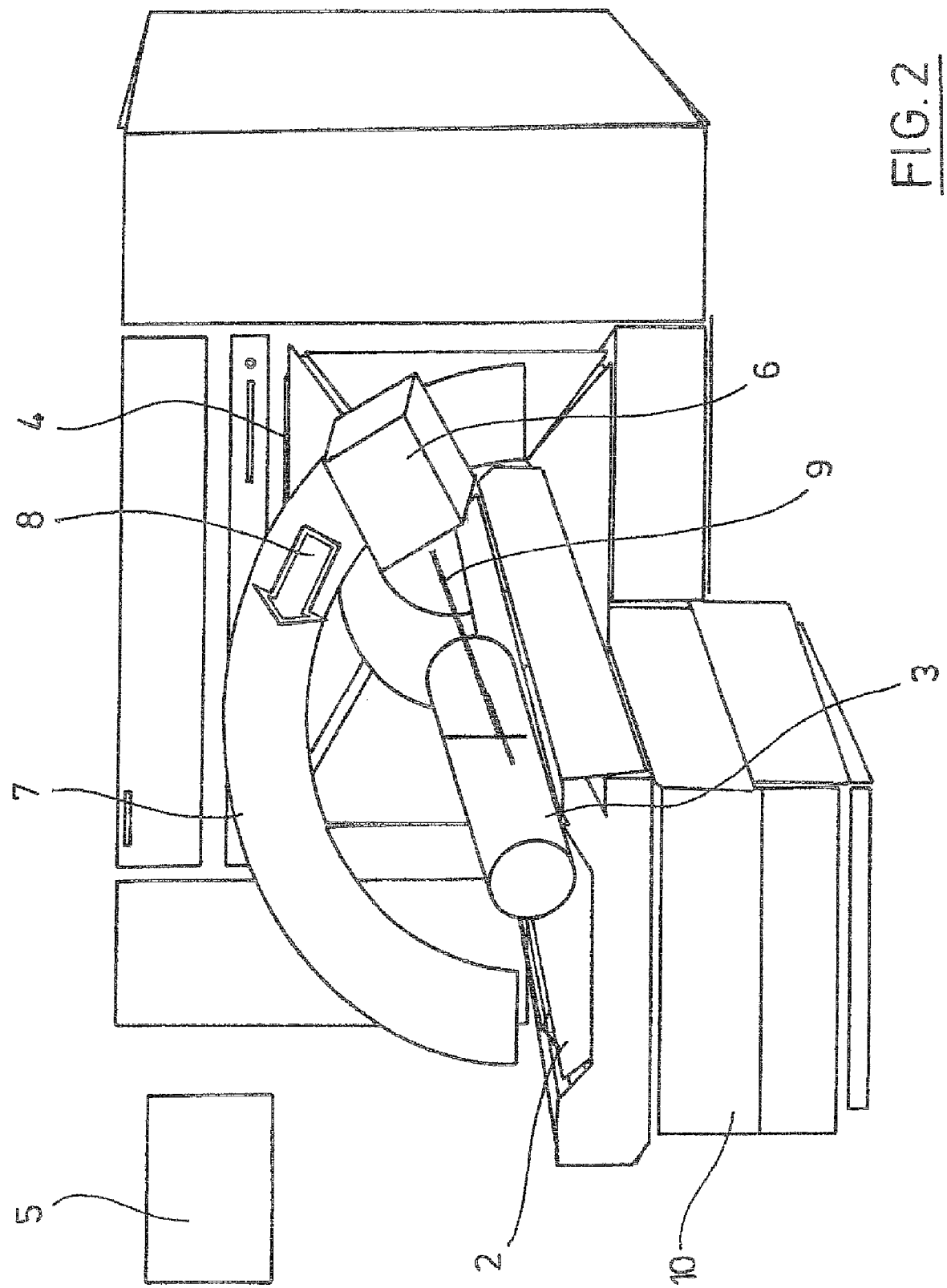

In FIG. 2, a further embodiment of the apparatus of the present invention is depicted. The same differs from that one of FIG. 1 only in that instead of two stationarily arranged projection devices 6, only one projection device 6 is provided which can be moved by means of adjustment drives, not shown in more detail, along a circular rail 7 running above the treatment table 2, as is schematically indicated by the arrow 8. In this, the respective holding position of the projection device 6 along the rail 7 can be selected by the control device 5 depending on the coordinates of the respective desired intersection area to be represented, and the adjustment drives can be addressed in a corresponding manner. With this embodiment, only one projection device 6 is necessary in order to be able to represent the desired intersection area on the entire surface of the patient's body 3.

Figure 3:
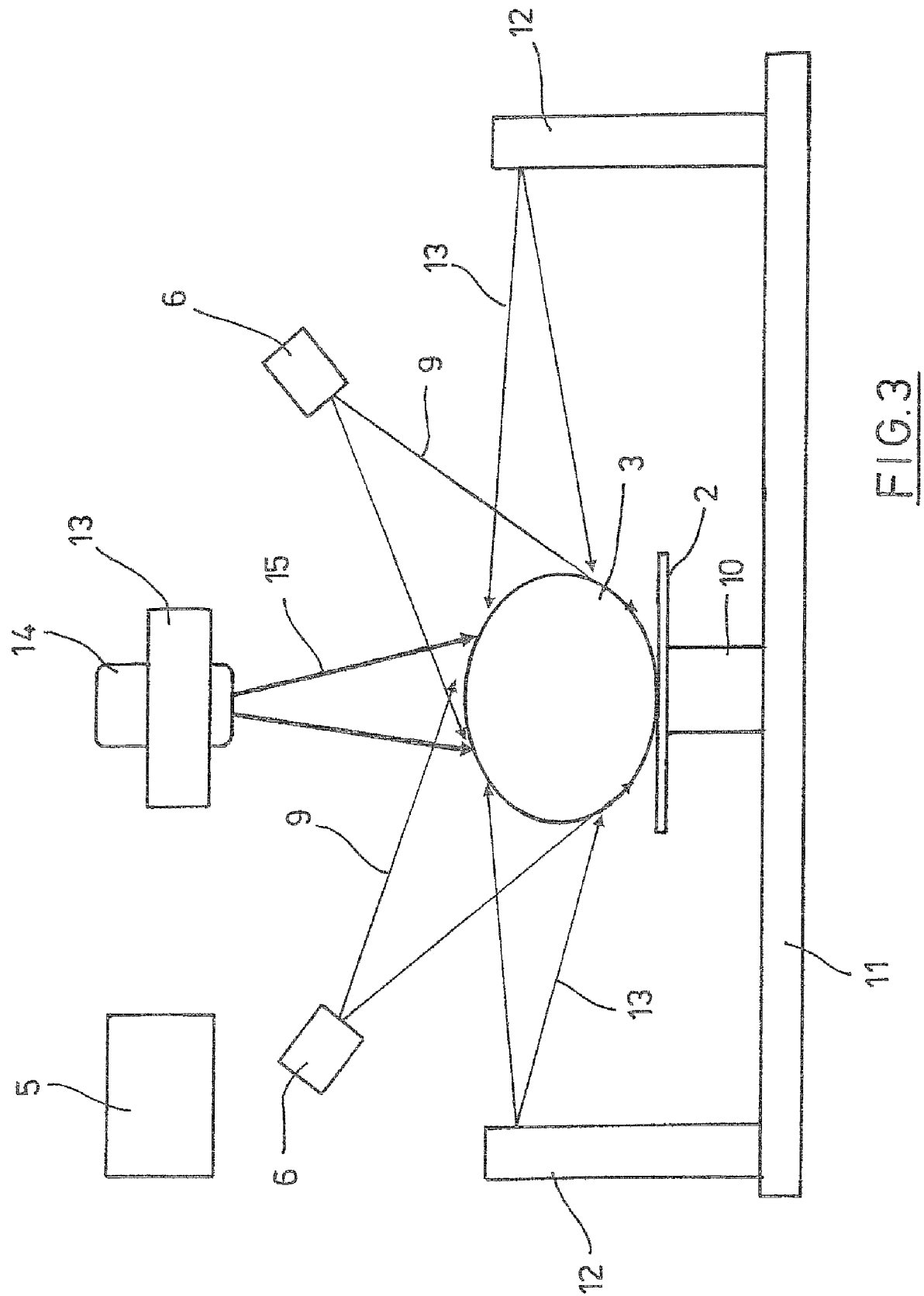

In FIG. 3, an apparatus of the present invention according to a further embodiment is depicted. According to this embodiment, two stationarily arranged projection devices 6 are arranged in the irradiation room used for the radiation therapy, together with the control device 5. Again, a patient's body 3 is shown very schematically on a positioning aid 2, which is supported on the floor 11 of the treatment room via a pedestal 10. Further, the apparatus in FIG. 3 has two lasers 12, arranged stationarily and opposite to each other on both sides of the patient's body 3. In a per se known manner, the same serve for positioning the patient's body 3 on the positioning aid 2 by means of marks arranged on the patient's body 3. Subsequently, a control of the positioning aid 2 takes place such that the patient's body 3 is moved into the preset position occupied during the radiation treatment.

Alternatively or in addition to the lasers 12, a laser scanning system 13, depicted only schematically in FIG. 3, or another system for acquiring the body surface may also be provided. Such a system, offered by the applicant under the name "Galaxy" for instance, has at least one laser scanner, by which a laser line not shown in more detail can be directed to the patient's body 3. Furthermore, the system 13 has a capturing device integrated into the system 13, by which the laser line reflected by the patient's body can be captured. The laser line is guided across the patient's body 3 by the system 13 successively, and the reflected light is measured by the capturing device. By means of suitable analysing algorithms, the topography of the patient's body 3 can be deduced and the same can be compared with a reference topography, for instance. The patient 3 can be moved into the desired position preset by the reference topography by a corresponding control of the adjustment drives of the support 2. Thus, a particularly accurate positioning of the patient 3 on the positioning aid 2 is ensured.

Furthermore, the apparatus depicted in FIG. 3 comprises an irradiation machine 14, in the present case a linear accelerator (LINAC). The irradiation machine 14 generates an ionising radiation for tumour treatment in the patient's body 3. In the apparatus according to FIG. 3, 3D coordinates of a desired intersection area provided by the control device 5 are forwarded again to the projection device 6 reaching the corresponding body region. The projection device 6 projects the desired intersection area with laser radiation 9 to the patient's body 3. In this, the projection of the desired intersection area takes place like already described referring to FIGS. 1 and 2. At the same time, a light radiation 15 corresponding to the ionising radiation generated by the irradiation machine is generated by the irradiation machine 14. This light radiation 15 generates a light intersection area on the patient's body 3, which corresponds to the intersection area of the ionising radiation to be generated by the irradiation machine 14 with the patient surface. By a comparison of the desired intersection area 18 projected to the patient body surface by the projection device 6 with the light intersection area generated by the irradiation machine 14, the correct alignment of the patient can now be checked. This will be explained in more detail by means of the schematic representation in FIG. 4.

Figure 4:
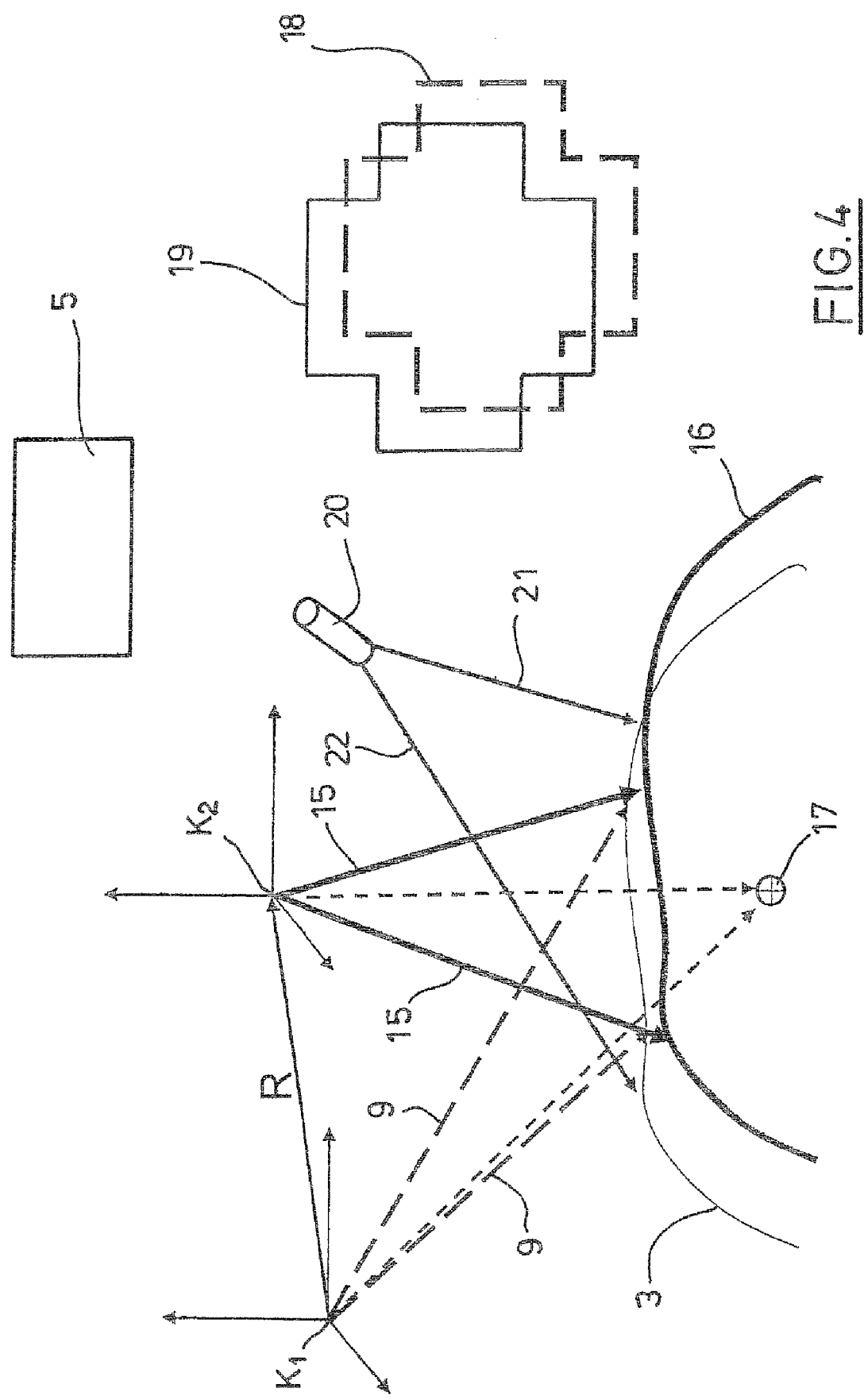

In FIG. 4, it can be recognised that different coordinate systems K1, K2 are valid for the projection device 6 and the irradiation machine 14. Their points of origin can be transformed into each other via a transformation vector R. The real patient's body 3 is distant from a desired position 16 of the patient's body 3 in the example depicted in FIG. 4. The isocentre for the irradiation is shown at 17 for the desired position 16 of the patient's body 3. Due to the deviation of the real patient's body 3 from the desired position 16, the desired intersection area 18 projected by the projection device 6 to the patient's body 3 and the light intersection area 19 radiated to the patient body surface by the irradiation machine 14 are not coincident, as is shown schematically in FIG. 4. Further, the apparatus has a sensor device 20, a camera 20 in the present case. The field of vision of the camera 20 is schematically represented by the arrows 21, 22. Thus, the camera 20 captures the desired intersection area 18 as well as the light intersection area 19. These captured data are transmitted via not shown lines to the analysing device integrated into the control device 5. By means of suitable image analysing algorithms, which are per se known, a deviation between the desired intersection area 18 and the light intersection area 19 is determined by the analysing device. In particular, the analysing device calculates a position of the positioning aid 2 for the patient's body 3 required for coincidence of the desired intersection area 18 and the light intersection area 19. Subsequently, the adjustment drives of the positioning aid 2 are addressed by the analysing device integrated into the control device 5 such that the positioning aid 2 is moved into the required position, so that the desired intersection area 18 and the light intersection area 19 are coincident. Now, the patient is in the desired position and the irradiation with the irradiation machine can begin.

Of course, the apparatus may further feature a real or nearly real time surface acquisition system, in order to adapt the projection of the desired intersection area depending on a surface of the patient's body 3 changed by the breathing of the patient, for instance.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An apparatus for the representation of an area on the three-dimensional surface of a patient's body, with a control device which provides three-dimensional coordinates of at least one area to be represented on the surface of the patient's body, wherein the area pre-sets a desired intersection area of a radiation area on the surface of the patient's body, characterized in that at least one projection device featuring a laser is provided, by which the desired intersection area can be projected to the three-dimensional surface of the patient's body on the basis of the provided coordinates, while at least one laser beam generated by the laser can be guided along the contour of the desired intersection area sufficiently rapidly, so that the impression of a closed contour around the desired intersection area results, further characterized in that an analyzing device is provided, which is designed to detect a deviation between the desired intersection area and the light intersection area.

2. An apparatus according to claim 1, characterized in that the projection device has at least two rotatable mirrors, by which the laser beam can be reflected to the surface of the patient's body and can be guided along the contour of the desired intersection area.

3. An apparatus according to claim 1, characterized in that a calibration of the projection device can be performed by means of the control device by providing calibration coordinates by means of the control device, and in that a calibration point or a projected calibration area, projected by the projection device with the provided calibration coordinates onto a surface, can be compared with a desired calibration point or a desired calibration area, respectively.

4. An apparatus according to claim 1, characterized in that it features an irradiation machine for generating an ionising radiation for the radiation therapy, wherein a light radiation corresponding to the radiation generated by the irradiation machine can be generated by the irradiation machine, and that the apparatus has a sensor device, by which the desired intersection area and a light intersection area of the light radiation of the irradiation machine can be acquired on the surface of the patient's body.

5. An apparatus according to claim 1, characterized in that it features a positioning aid accommodating the patient's body, mounted adjustably along at least three degrees of freedom by means of suitable adjustment drives.

6. An apparatus according to the claim 1, characterized in that the analyzing device is designed to determine a position of the positioning aid necessary for the coincidence between the desired intersection area and the light intersection area.

7. An apparatus according to claim 6, characterized in that the analyzing device is designed to control the adjustment drives such that the positioning aid is moved into the necessary position.

8. An apparatus according to claim 5, characterized in that a device for determining the topography of a patient's body present on the positioning aid is provided, which has at least one laser scanner by which a laser line can be directed to the patient's body, and at least one capture device, by which the laser line reflected by the patient's body can be captured.

9. An apparatus according to claim 8, characterized in that a topography analyzing device is provided, which is designed to determine the topography of the patient's body from the data acquired by the capture device, to compare it with a desired topography and to determine a position of the positioning aid necessary for the coincidence between the measured topography and the desired topography by means of the comparison.

10. An apparatus according to claim 1, characterized in that the projection device is arranged to be movable along a substantially circular course around a positioning aid accommodating the patient's body.

11. An apparatus according to claim 1, characterized in that it has a device for determining a three-dimensional surface shape of a patient's body situated on the positioning aid in real time or nearly real time, wherein three-dimensional surface data determined by the device can be forwarded to the control device in real time or nearly real time.

12. An apparatus according to claim 11, characterized in that the device for determining the three-dimensional surface shape of the patient's body in real time or nearly real time features at least one laser, by which at least one laser line can be directed to the patient's body, and at least one matrix sensor, by which the laser line reflected by the patient's body can be detected.

13. An apparatus according to claim 8, characterized in that the control device is designed to address the projection device such that the same projects the desired intersection area to the three-dimensional surface of the patient's body only in a pre-set surface position of the patient's body.

14. An apparatus according to claim 11, characterized in that the control device is designed to adapt the coordinates of the desired intersection area provided to the projection device depending on the respective surface of the patient's body in real or nearly real time, such that the projected intersection area represents the desired intersection area of the therapy area envisioned for the radiation therapy with the surface of the patient's body at any time.

15. A method for the representation of an area on the three-dimensional surface of a patient's body, wherein three-dimensional coordinates of at least one area to be represented on the surface of the patient's body are provided by a control device, wherein the area pre-sets a desired intersection area of a radiation area on the surface of the patient's body, characterized in that with at least one projection device featuring a laser, the desired intersection area is projected to the three-dimensional surface of the patient's body on the basis of the provided coordinates, while at least one laser beam generated by the laser is guided along the contour of the desired intersection area sufficiently rapidly, so that the impression of a close contour around the desired intersection area results, further characterized in that an analyzing device is provided, which is designed to detect a deviation between the desired intersection area and the light intersection area.

16. A method according to claim 15, characterized in that the laser beam is reflected to the surface of the patient's body by at least two rotatable mirrors and is guided along the contour of the desired intersection area.

17. A method according to claim 15, characterized in that a calibration of the projection device is performed by providing calibration coordinates, and a calibration point or a projected calibration area, projected by the projection device onto a surface based on the provided calibration coordinates, is compared with a desired calibration point or a desired calibration area, respectively.

18. A method according to claim 15, characterized in that with an irradiation machine for generating an ionising radiation for the radiation therapy, a light radiation corresponding to the radiation generated by the irradiation machine is generated, and that the desired intersection area and a light intersection area of the light radiation of the irradiation machine on the surface of the patient's body is acquired.

19. A method according to claim 18, characterized in that a deviation between the desired intersection area and the light intersection area is detected.

20. A method according to claim 19, characterized in that a position of the adjustably mounted positioning aid accommodating the patient's body necessary for the coincidence between the desired intersection area and the light intersection area is determined.

21. A method according to claim 20, characterized in that the positioning aid is moved into the necessary position.

22. A method according to claim 15, characterized in that for determining the topography of a patient's body present on an adjustably mounted positioning aid, a laser line is directed to the patient's body, and that the laser line reflected by the patient's body is captured.

23. A method according to claim 22, characterized in that the topography of the patient's body is determined from the captured data, is compared with a desired topography and a position of the positioning aid necessary for the coincidence between the measured topography and the desired topography is determined by means of the comparison.

24. A method according to claim 15, characterized in that the three-dimensional surface shape of a patient's body is determined in real time or nearly real time, and the determined three-dimensional surface data are forwarded to the control device in real time or nearly real time.

25. A method according to claim 24, characterized in that in order to determine the surface shape of the patient's body in real time or nearly real time, at least one laser line is directed to the patient's body, and the laser line reflected by the patient's body is detected by at least one matrix sensor.

26. A method according to claim 24, characterized in that the projection device is controlled such that the same projects the desired intersection area to the three-dimensional surface of the patient's body only in a pre-set surface position of the patient's body.

27. A method according to claim 24, characterized in that the control device adapts the coordinates of the desired intersection area provided to the projection device depending on the respective surface of the patient's body in real or nearly real time such that the projected intersection area represents the desired intersection area of the therapy area envisioned for the radiation therapy with the surface of the patient's body at any time.

* * * * *